US00PP09359P

United States Patent [19]

Bradford et al.

[11] Patent Number: Plant 9,359

[45] Date of Patent: Nov. 7, 1995

[54] NECTARINE TREE 'BRIGHT PEARL'

[76] Inventors: Lowell G. Bradford, 12439 E. Savana Rd.; Norman G. Bradford, 11875 E. Savana Rd., both of Le Grand, Calif. 95333

[21] Appl. No.: 383,905

[22] Filed: Feb. 6, 1995

[51] Int. Cl.[6] ..... A01H 5/00

[52] U.S. Cl. ..... Plt./40.1

[58] Field of Search ..... Plt./40.1

[56] References Cited

U.S. PATENT DOCUMENTS

| | | | |
|---|---|---|---|
| P.P. 6,363 | 11/1988 | Bradford et al. | Plt./41 |
| P.P. 7,193 | 3/1990 | Bradford et al. | Plt./41 |
| P.P. 8,461 | 11/1993 | Bradford et al. | Plt./40.1 |

*Primary Examiner*—James R. Feyrer

[57] ABSTRACT

The present invention relates to a nectarine tree and more particularly to a new and distinct variety broadly characterized by a large size, vigorous, productive and regular bearing tree. The fruit matures under the ecological conditions described approximately the third week in July, with first picking on Jul. 22, 1994. The fruit is uniformly large in size, non-acidic in flavor, globose in shape, clingstone in type, very firm in texture, and nearly full red in skin color. The variety was a first generation cross using Red Glen (U.S. Plant Pat. No. 7,193) yellow flesh nectarine as the selected seed parent and an unnamed white flesh nectarine seedling as the selected pollen parent, which was previously developed by crossing August Red (U.S. Plant Pat. No. 6,363) nectarine by Bradcrim (U.S. Plant Pat. No. 8,461) nectarine.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as "Bright Pearl". The present variety was developed by us in 1991 in a cultivated area of our experimental orchard at Bradford Farms near Le Grand, Calif. in Merced County (San Joaquin Valley). It was a first generation cross using Red Glen (U.S. Plant Pat. No. 7,193) nectarine as the seed parent and an unnamed white flesh nectarine seedling as the selected pollen parent. This unnamed pollen parent was previously developed by crossing August Red (U.S. Plant Pat. No. 6,363) nectarine by Bradcrim (U.S. Plant Pat. No. 8,461) nectarine. Subsequent to origination of the present variety of nectarine tree, we asexually reproduced it by budding and grafting, and such reproduction of plant and fruit characteristics were true to the original plant in all respects.

The fruit produced by the present variety is most similar to its pollen grandparent, the Bradcrim (U.S. Plant Pat. No. 8,461), by producing white flesh nectarines that are non-acidic in flavor and virtually free from red texture bleeding, but is distinguished therefrom and an improvement thereon by producing fruit that ripens twenty-three days later, that is larger in size, that is fuller red in skin color, that is much firmer in texture, that is much sweeter in flavor, and that is clingstone instead of freestone.

The present variety is similar to both its seed parent, Red Glen (U.S. Plant Pat. No. 7,193) and its pollen grandparent, August Red (U.S. Plant Pat. No. 6,363), by producing nectarines that are large sized, clingstone, very firm, and nearly full red in skin color, but is very distinguished from both by producing fruit that is white flesh instead of yellow flesh, and that is non-acidic in flavor instead of acidic.

DRAWING

The accompanying photograph exhibits four whole fruits positioned to display the characteristics of the skin color and form, one fruit divided transversely to the suture plane to reveal the flesh and stone, a stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on Jul. 27, 1994 . All major color code designations are by reference to the Inter-Society Color Council, National Bureau of Standards. Common color names are also used occasionally.

TREE

Size: Large.
Vigor: Vigorous.
Growth: Spreading and dense.
Form: Round topped.
Hardiness: Hardy.
Production: Very productive.
Bearing: Regular bearer.
Trunk:
- *Size.*—Medium.
- *Texture.*—Medium.
- *Bark color.*—Brownish gray [64. brGy] .
- *Lenticels.*—Numerous. Color: Dark orange yellow [72. d.OY]. Average size: 3/16" to 3/8" [ 4.8–9.5 mm.].

Branches:
- *Size.*—Medium.
- *Texture.*—Medium.
- *Color.*—1st year wood topside: Grayish pink [8. gy.Pk] when exposed to sun. 1st year wood underside: Light yellow green [119. l.YG]. Older wood: Moderate brown [58. m.Br].
- *Lenticels.*—Numerous, medium. Color: Deep orange yellow [69. deep OY]. Average size: 1/8" [3.2 mm.].

Leaves:
- *Size.*—Medium. Average length: 5¼" [133.4 mm.]. Average width: 1½" [38.1 mm.].
- *Thickness.*—Medium.

*Form.*—Elliptical.
*Apex.*—Acuminate.
*Base.*—Acute.
*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: ½" [12.7 mm.]. Average thickness: 1/16" [1.6 mm.]. Dorsal color: Brilliant yellow green [116. brill.YG]. Ventral color: Light yellow green [119. l.YG].
*Stipules.*—Numerous. Average length: 3/16" to ¼" [4.8–6.4 mm.].
*Glands.*—Numbers: 2 per leaf. Position: Slightly alternately positioned on petiole and base of blade. Size: Small. Form: Globose. Color: Light yellow green [119. l.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium as compared with other varieties.
*Size.*—Large.
*Color.*—Moderate pink [5. m.Pk].

FRUIT

Maturity when described: Hard ripe, Jul. 27, 1994.
Date of first picking: Jul. 22, 1994.
Date of last picking: Jul. 31, 1994.
Size: Uniform, large.
*Average diameter axially.*—2 11/16" [68.3 mm.].
*Average transversely in suture plane.*—2¾" [69.9 mm.].
Form: Globose, uniform, mostly symmetrical but few unsymmetrical.
*Longitudinal section form.*—Circular to obovate.
*Transverse section through diameter.*—Circular.
Suture: An inconspicuous line extending from the base to slightly beyond the apex, having a slight depression beyond the pistil point.
Ventral surface: Rounded, lipped throughout but stronger on one side.
Lips: Unequal.
Cavity: Flaring, circular, suture showing on one side.
*Depth.*—⅜" [9.5 mm.].
*Breadth.*—⅞" [22.2 mm.].
Base: Rounded and truncate.
Apex: Rounded.
Pistil point: Negligible in length, mostly oblique and depressed within the suture.
Stem: Medium.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—None observed.
*Color.*—Very dark red [17. v.d.R] blending to deep red [13. deep R] over 90% of surface with pale orange yellow [73. p.OY] frecking toward the apex, with sun protected areas having pale yellow green [121. p.YG] background.

Flesh:
*Color.*—White [263. White] to pale yellow green [121. p.YG] with some deep red [13. deep R] streaking very near the stone.
*Surface of pit cavity.*—Deep red [13. deep R].
*Amygdalin.*—Wanting.
*Juice.*—Abundant, rich.
*Texture.*—Extremely firm, tough, non-melting.
*Fibers.*—Abundant, fine.
*Ripens.*—Evenly, slightly earlier at apex and lips.
*Flavor.*—Non-acidic and very sweet, with 18 to 20 brix.
*Aroma.*—Moderate.
*Eating quality.*—Very best.

STONE

Type: Clingstone.
Form: Oval to obvoid.
Base: Straight.
Apex: Acuminate.
Sides: Slightly unequal.
Surface: Horizontally furrowed toward the apex and some pitting toward the base.
Ridges: Jagged toward the base.
Color: Moderate reddish brown [43. m.rBr] on the outside, light reddish brown [42. l.rBr] on the inside.
Pit wall: 7/32" [5.6 mm.] thick.
Tendency to split: Very slight.
Kernel:
*Form.*—Oval.
*Taste.*—Bitter.
*Viable.*—Yes.
*Average width.*—9/16" [14.3 mm.].
*Average length.*—13/16" [20.6 mm.].
*Skin color.*—Deep orange yellow [69. deep OY] with grayish brown [61. gy.Br] veins or lines running from the pellicle to the apex.
*Pellicle color.*—Grayish brown [61. gy.Br].
*Amygdalin.*—Abundant.

USE

Market: Fresh and long distance shipping.
Keeping quality: Very good.
Shipping quality: Very good.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen grandparent, the Bradcrim (U.S. Plant Pat. No. 8,461) nectarine, by producing white flesh nectarines that are non-acidic in flavor and virtually free from red texture bleeding, but is distinguished therefrom and an improvement thereon by producing fruit that ripens twenty-three days later, that is larger in size, that is fuller red in skin color, that is much firmer in texture, that is much sweeter in flavor, and that is clingstone instead of freestone.

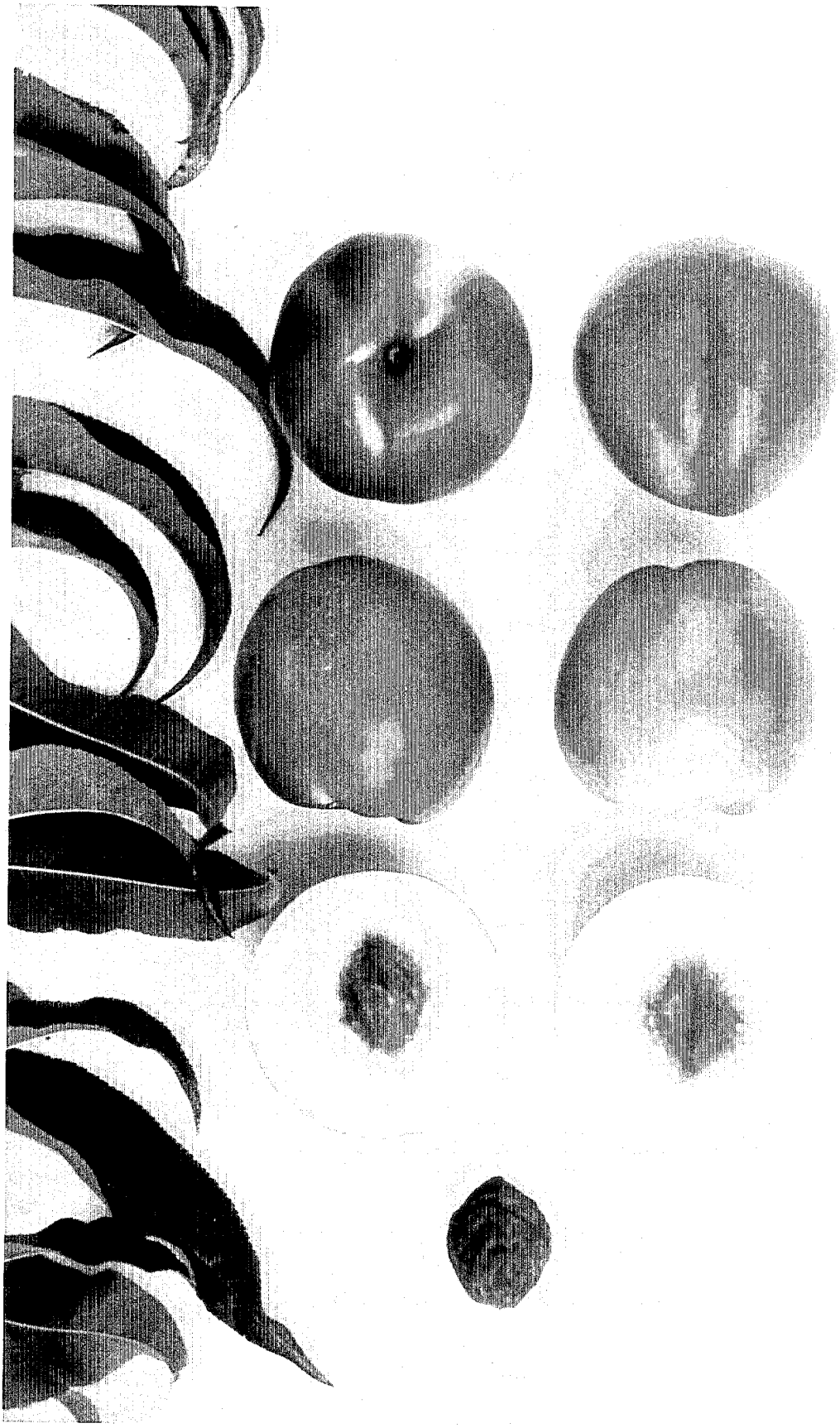

* * * * *